(12) United States Patent
Ding et al.

(10) Patent No.: US 6,284,305 B1
(45) Date of Patent: Sep. 4, 2001

(54) DRUG COATING WITH TOPCOAT

(75) Inventors: Ni Ding, Plymouth, MN (US); Michael N. Helmus, Long Beach, CA (US)

(73) Assignee: Schneider (USA) Inc., Plymouth, MN (US)

(*) Notice: Subject to any disclaimer, the term of this patent is extended or adjusted under 35 U.S.C. 154(b) by 0 days.

(21) Appl. No.: 09/573,506

(22) Filed: May 18, 2000

Related U.S. Application Data (60) Division of application No. 08/996,410, filed on Dec. 22, 1997, now Pat. No. 6,099,562, which is a continuation-in-part of application No. 08/663,518, filed on Jun. 13, 1996, now Pat. No. 6,120,536.

(51) Int. Cl.[7] ................................................. A61L 13/00
(52) U.S. Cl. ..................... 427/2.28; 427/2.24; 427/2.3; 427/409; 427/261; 427/407.1
(58) Field of Search ................................ 427/2.24, 2.25, 427/2.28, 2.3, 409, 261, 407.1

(56) References Cited

U.S. PATENT DOCUMENTS

| | | |
|---|---|---|
| 3,932,627 | 1/1976 | Margraf . |
| 4,292,965 | 10/1981 | Nash et al. . |
| 4,613,665 | 9/1986 | Larm . |
| 4,655,771 | 4/1987 | Wallsten . |
| 4,872,867 | 10/1989 | Joh et al. . |
| 4,886,062 | 12/1989 | Wiktor . |
| 4,916,193 | 4/1990 | Tang et al. . |

(List continued on next page.)

FOREIGN PATENT DOCUMENTS

| | | |
|---|---|---|
| 0623354 | 11/1994 | (EP) . |
| 0734721 | 10/1996 | (EP) . |
| WO 91/12779 | 9/1991 | (WO) . |
| WO 92/15286 | 9/1992 | (WO) . |
| WO 94/21308 | 9/1994 | (WO) . |
| WO 94/21309 | 9/1994 | (WO) . |
| WO 9600272 | 6/1996 | (WO) . |

OTHER PUBLICATIONS

Baxter Healthcare Corp. Duralo Biocompatible Treatment.
Ludwig K. von Segesser, MD., "Heparin–Bonded Surfaces in Extracorporeal Membrane Oxygenation for Cardiac Support", The Society of Thoracic Surgeons, (1996).
Li–Chien Hsu, "Principles of Heparin–Coating Techniques", Perfusion 6: 209–219 (1991).

(List continued on next page.)

*Primary Examiner*—Shrive Beck
*Assistant Examiner*—Jennifer Kolb (57) ABSTRACT

A coating and method for a coating an implantable device or prostheses are disclosed. The coating includes an undercoat of polymeric material containing an amount of biologically active material, particularly heparin, dispersed therein. The coating further includes a topcoat which covers less than the entire surface of the undercoat and wherein the topcoat comprises a polymeric material substantially free of pores and porosigens. The polymeric material of the topcoat can be a biostable, biocompatible material which provides long term non-thrombogenicity to the device portion during and after release of the biologically active material.

12 Claims, 9 Drawing Sheets

U.S. PATENT DOCUMENTS

| | | |
|---|---|---|
| 4,954,126 | 9/1990 | Wallsten . |
| 4,994,071 | 2/1991 | McGregor . |
| 5,019,096 * | 5/1991 | Fox, Jr. et al. ............................ 623/1 |
| 5,061,275 | 10/1991 | Wallsten et al. . |
| 5,092,877 | 3/1992 | Pinchuk . |
| 5,163,952 | 11/1992 | Froix . |
| 5,180,366 | 1/1993 | Woods . |
| 5,182,317 | 1/1993 | Winters et al. . |
| 5,185,408 | 2/1993 | Tang et al. . |
| 5,226,913 | 7/1993 | Pinchuk . |
| 5,258,020 | 11/1993 | Froix . |
| 5,262,451 | 11/1993 | Winters et al. . |
| 5,292,802 | 3/1994 | Rhee et al. . |
| 5,304,121 | 4/1994 | Sahatjian . |
| 5,308,889 | 5/1994 | Rhee et al. . |
| 5,318,779 * | 6/1994 | Hakamatsuka et al. ............. 424/426 |
| 5,338,770 | 8/1994 | Winters et al. . |
| 5,342,348 | 8/1994 | Kaplan . |
| 5,356,433 | 10/1994 | Rowland et al. . |
| 5,380,299 | 1/1995 | Fearnot et al. . |
| 5,415,619 | 5/1995 | Lee et al. . |
| 5,419,760 | 5/1995 | Narciso, Jr. . |
| 5,429,618 | 7/1995 | Keogh . |
| 5,447,724 | 9/1995 | Helmus et al. . |
| 5,449,382 | 9/1995 | Dayton . |
| 5,464,650 | 11/1995 | Berg et al. . |
| 5,543,155 * | 8/1996 | Fekete et al. ........................ 424/473 |
| 5,545,208 | 8/1996 | Wolff et al. . |
| 5,624,411 | 4/1997 | Tuch . |
| 5,637,113 * | 6/1997 | Tartaglia et al. ......................... 623/1 |
| 5,716,981 | 2/1998 | Hunter et al. . |
| 5,749,915 * | 5/1998 | Slepian .................................... 623/1 |
| 5,980,972 * | 11/1999 | Ding ................................... 427/2.24 |
| 6,042,875 * | 3/2000 | Ding et al. .......................... 427/2.24 |
| 6,110,483 * | 8/2000 | Whitbourne et al. ................ 424/423 |
| 6,198,016 * | 3/2001 | Lucast et al. .......................... 602/41 |

OTHER PUBLICATIONS

J.M. Toomasian et al., "Evaluation of Duraflo II Heparin Coating in Prolonged Extracorporeal Membrane Oxygenation", ASAIO Trans 34: 410–14 (1988).

S.D. Tong et al., "Non–Thrombogenic Hemofiltration System for Acute Renal Failure Treatment", ASAIO Trans. 38: M702–M706 (1992).

Bergstrom, Reduction of fibrinogen adsorption on PEG––coated polystyrene surfaces, 1992, p. 779–790, Baxter Healthcare Corp. Duraflo Biocompatible Treatment.

Michael N. Helmus, "Medial Device Design—A Systems Approach: Central Venous Catheters", (1990).

Polysciences Inc., TDMAC–Heparin Coatings, Nov. 1988, Data Sheet #172.

Barbucci, et al., Coating of Commercially available materials with a new heparinizable material, 1991, pp. 1259–1274.

Michael N. Helmus, Grant Application–Ionic–Hydrophilic Density: Platelet/Monocyte Adherence Dec. 1981 Dec. 1984, pp. 13, 14, 26–31.

Dennis E. Chenoweth, Complement Activation in Extracorporeal Circuits, pp. 306–329.

Jeffrey A. Hubbell, Ph.D., Jul.–Sep.–1993 Pharmacologic Modification of Materials, 1215–1275.

Glenn P. Gravlee, MD, Heparin–Coated Cardiopulmonary Bypass Circuits, Journal of Cardiothoracic and Vascular Anesthesia, vol. 8, No. 2, Apr. 1994, pp. 213–222.

K. Isihara, H. Hanyuda, and N. Nakabayashi, Synthesis of phospholipid polymers having a urethane bond..., Biomaterials, 1995, pp. 873–879.

J. Sanchez, G. Elgue, J. Riesenfeld and P. Olsson, Control of Contact activation on end–point immobilized heparin, The role of antithrombin and the specific antithrombin–binding sequence, 1995, pp. 655–661, Journal of Biomedical Materials Research.

Cardiology Conference European Society of Cardiology Conference Clinica, Sep. 4, 1995, pp. 24–26.

Mansoor Amiji and Kinam Park, "Surface Modification of Polymeric Materials with Poly (ethylene oxide), Albumin, and Heparin for Reduced Thrombogenicity," Purdue University, School of Pharmacy, West Lafayette, IN, 47907.

* cited by examiner

Figure 1

Figure 2. Release profile for multilayer system

× Tie Layer = 37.5% Hep coating, top layer = silicone
■ Tie Layer = 37.5% Hep coating, top layer = 16.7% Hep coating
+ Single Layer = 37.5% Hep coating Figure 3. Release profile for multilayer system + Tie Layer = 37.5% Hep coating, top layer = silicone
■ Tie Layer = 37.5% Hep coating, top layer = 16.7% Hep coating Figure 4. Release kinetics for different drug loading at the similar coating thickness Figure 5. Drug elution kinetics at different coating thickness (A ~ 10-15um). Drug loading = 41.1%

Figure 6. 37.5% Hep in tie-coat with the same tie-coat thickness and 16.7% Hep in top-coat Figure 8. Comparison of fluorosilicone (FSI) top coat w or w/o heparin. The thickness of the tie coat (37.5%) heparin is about 40 micron.

FIG. 9

DRUG COATING WITH TOPCOAT

CROSS-REFERENCE TO RELATED APPLICATIONS

The present application is a divisional application of application Ser. No. 08/996,410, filed Dec. 22, 1997, and now U.S. Pat. No. 6,099,562, which is a continuation-in-part application of application Ser. No. 08/663,518, filed Jun. 13, 1996, now U.S. Pat. No. 6,120,536.

BACKGROUND OF THE INVENTION

1. Field of the Invention

The present invention relates generally to providing biostable elastomeric coatings on the surfaces of implants which incorporate biologically active species having controlled release characteristics in the coating and relates particularly to providing a non-thrombogenic surface during and after timed release of the biologically active species. The invention is particularly described in terms of coatings on therapeutic expandable stent prostheses for implantation in body lumens, e.g., vascular implantation.

2. Related Art

In surgical or other related invasive procedures, the insertion and expansion of stent devices in blood vessels, urinary tracts or other locations difficult to otherwise access for the purpose of preventing restenosis, providing vessel or lumen wall support or reinforcement and for other therapeutic or restorative functions has become a common form of long-term treatment. Typically, such prostheses are applied to a location of interest utilizing a vascular catheter, or similar transluminal device, to carry the stent to the location of interest where it is thereafter released to expand or be expanded in situ. These devices are generally designed as permanent implants which may become incorporated in the vascular or other tissue which they contact at implantation.

One type of self-expanding stent has a flexible tubular body formed of several individual flexible thread elements each of which extends in a helix configuration with the centerline of the body serving as a common axis. The elements are wound in the same direction but are displaced axially relative to each other and meet, under crossing a like number of elements also so axially displaced, but having the opposite direction of winding. This configuration provides a resilient braided tubular structure which assumes stable dimensions upon relaxation. Axial tension produces elongation and corresponding diameter contraction that allows the stent to be mounted on a catheter device and conveyed through the vascular system as a narrow elongated device. Once tension is relaxed in situ, the device at least substantially reverts to its original shape. Prostheses of the class including a braided flexible tubular body are illustrated and described in U.S. Pat. Nos. 4,655,771 and 4,954,126 to Wallsten and U.S. Pat No. 5,061,275 to Wallsten et al.

Implanted stents have been used to carry medicinal agents, such as thrombolytic agents. U.S. Pat. 5,163,952 to Froix discloses a thermalmemoried expanding plastic stent device formulated to carry a medicinal agent in the material of the stent itself. Pinchuk, in U.S. Pat. No. 5,092,877, discloses a stent of a polymeric material which may have a coating associated with the delivery of drugs. Other patents which are directed to devices of the class utilizing biodegradable or bio-sorbable polymers include Tang et al., U.S. Pat. No. 4,916,193, and MacGregor, U.S. Pat. No. 4,994,071.

A patent to Sahatjian, U.S. Pat. No. 5,304,121, discloses a coating applied to a stent consisting of a hydrogel polymer and a preselected drug such as a cell growth inhibitors or heparin. A further method of making a coated intravascular stent carrying a therapeutic material is described in Berg et al., U.S. Pat. No. 5,464,650, issued on Nov. 7, 1995 and corresponding to European Patent Application No. 0 623 354 A1 published Nov. 9, 1994. In that disclosure, a polymer coating material is dissolved in a solvent and the therapeutic material dispersed in the solvent; the solvent evaporated after application.

An article by Michael N. Helmus (a co-inventor of the present invention) entitled "Medical Device Design—A Systems Approach: Central Venous Catheters", 22nd International Society for the Advancement of Material and Process Engineering Technical Conference (1990) relates to polymer/drug/membrane systems for releasing heparin. Those polymer/drug/membrane systems require two distinct types of layers to function.

It has been recognized that contacting blood with the surface of a foreign body in vivo has a tendency to induce thrombogenic responses and that as the surface area of a foreign device in contact with host blood increases, the tendency for coagulation and clot forming at these surfaces also increases. This has led to the use of immobilized systemic anti-coagulant or thrombolytic agents such as heparin on blood contacting surfaces such as oxygen uptake devices to reduce this phenomenon. Such an approach is described by Winters, et al., in U.S. Pat. Nos. 5,182,317; 5,262,451 and 5,338,770 in which the amine functional groups of the active material are covalently bonded using polyethylene oxide (PEO) on a siloxane surface.

Another approach is described in U.S. Pat. No. 4,613,665 to Larm in which heparin is chemically covalently bound to plastic surface materials containing primary amino groups to impart a non-thrombogenic surface to the material. Other approaches for bonding heparin are described in Barbucci, et al., "Coating of commercially available materials with a new heparinizable material", *Journal of Biomedical Materials Research*, Vol. 25, pp. 1259–1274 (1991); Hubbell, J. A., "Pharmacologic Modification of Materials", *Cardiovascular Pathology*, Vol. 2, No. 3 (Suppl.), 121S–127S (1993); Gravlee, G. P., "Heparin-Coated Cardiopulmonary Bypass Circuits", *Journal of Cardiothoracic and Vascular Anesthesia*, Vol. 8, No. 2, pp. 213–222 (1994).

Moreover, drug elution rates for a coating containing a hydrophilic or a lipophobic drug is usually very fast initially when the coated device contacts body fluid or blood. One of the methods to reduce the so called "burst effect" is to add a membrane containing porosigen over the coating layer containing the biologically active material. See e.g., U.S. Pat. No. 5,605,696 to Eury et al. and U.S. Pat. No. to Helmus et al. U.S. Pat. No. 5,447,724. When the porosigen elutes, a porous membrane is formed and the drug in the undercoat will release. Even though the method might be quite successful to control the drug release, it increases the coating thickness, reduces the effective drug loading and introduces undesirable additional foreign materials into the patient. Hence, there is a need for a coating which reduces the burst effect but is not too thick and does not require the release of porosigens into the body.

With regard to stents, polymeric stents, although effective, may have mechanical properties that are inferior to those of metal stents of like thickness and weave. Metallic vascular stents braided of even relatively fine metal can provide a large amount of strength to resist inwardly directed circumferential pressure. A polymer material of comparable strength requires a much thicker-walled structure or heavier, denser filament weave, which in turn, reduces the cross-sectional area available for flow through the stent and/or reduces the relative amount of opens space in the weave. Also, it is usually more difficult to load and deliver polymeric stents using catheter delivery systems.

While certain types of stents such as braided metal stents may be preferred for some applications, the coating and coating modification process of the present invention is not so limited and can be used on a wide variety of prosthetic devices. Thus, in the case of stents, the present invention also applies, for example, to the class of stents that are not self-expanding, including those which can be expanded, for instance, with a balloon; as well as polymeric stents of all kinds. Other medical devices that can benefit from the present invention include blood exchanging devices, vascular access ports, central venus catheters, cardiovascular catheters, extracorpeal circuits, vascular grafts, pumps, heart valves, and cardiovascular sutures, to name a few. Regardless of detailed embodiments, applicability of the invention should not be considered limited with respect to implant design, implant location or materials of construction. Further, the present invention may be used with other types of implantable prostheses.

Accordingly, it is a primary object of the present invention to provide a coating and process for coating a stent to be used as a deployed stent prostheses, the coating being capable of effective controlled long-term delivery of biologically active materials.

Another object of the invention is to provide a coating and process for coating a stent prostheses using a biostable hydrophobic elastomer in which biologically active species are incorporated within a coating.

Still another object of the present invention is to provide a multi-layer coating and process for the delivery of biologically active species in which the percentage of active material can vary from layer to layer.

Yet another object of the present invention is to provide a multi-layer coating and process for the delivery of biologically active species from a coating with a non-thrombogenic surface.

Another object of the invention is to provide a coating for the delivery of biologically active species having a top layer or topcoat which reduces the initial release of the species, in which the topcoat is substantially free of pores or porosigens and covers less than the entire surface of the undercoat. The topcoat can cover less than the entire surface of the undercoat before and/or while the device is implanted.

A further object of the invention is to provide a multilayer coating for the delivery of biologically active species such as heparin having a fluorosilicone top layer.

A still further object of the invention is to provide a multi-layer coating for the delivery of biologically active species such as heparin having a surface containing immobilized polyethylene glycol (PEG).

Other objects and advantages of the present invention will become apparent to those skilled in the art upon familiarization with the specification and appended claims.

SUMMARY OF THE INVENTION

The present invention provides a relatively thin layered coating of biostable elastomeric material containing an amount of biologically active material dispersed therein in combination with a non-thrombogenic surface that is useful for coating the surfaces of prostheses such as deployable stents.

The preferred stent to be coated is a self-expanding, open-ended tubular stent prostheses. Although other materials, including polymer materials, can be used, in the preferred embodiment, the tubular body is formed of a self expanding open braid of fine single or polyfilament metal wire which flexes without collapsing, readily axially deforms to an elongate shape for transluminal insertion via a vascular catheter and resiliently expands toward predetermined stable dimensions upon removal in situ.

In the process, the initial coating is preferably applied as a mixture, solution or suspension of polymeric material and finely divided biologically active species dispersed in an organic vehicle or a solution or partial solution of such species in a solvent or vehicle for the polymer and/or biologically active species. For the purpose of this application, the term "finally divided" means any type or size of included material from dissolved molecules through suspensions colloids and particulate mixtures. The biologically active material is dispersed in a carrier material which may be the polymer, a solvent, or both. The coating is preferably applied as a plurality of relatively thin layers sequentially applied in relatively rapid sequence and is preferably applied with the stent in a radially expanded state.

In many applications the layered coating is referred to or characterized as including an undercoat and topcoat. The coating thickness ratio of the topcoat to undercoat may vary with the desired effect and/or the elution system. Typically these are of different formulations with most or all of the biologically active material being contained in the undercoat and a non-thrombogenic or biocompatible non-porous surface found in the topcoat.

It is desirable that the topcoat be substantially free of connected pores or porosigens (materials which can elute during implantation and form pores). The addition of a porous membrane as a top coat will increase the coating thickness and reduce the overall drug loading. Also, the release of porosigens into the body can be undesirable since it introduces additional foreign materials into the body, which can cause the patient to have adverse reactions.

Since in some embodiments the topcoat should be substantially free of pores, the topcoat should cover less than the entire surface of the undercoat. Preferably, the topcoat should cover only about 10% to about 95% of the surface of the undercoat.

By partially covering the surface during manufacture or inducing "breaks" in the topcoat during mounting/implanting of the coated device, the biologically active material or drug of the undercoat is permitted to be released from the undercoat through those parts of the undercoat which are not covered by the topcoat.

Figure 9:
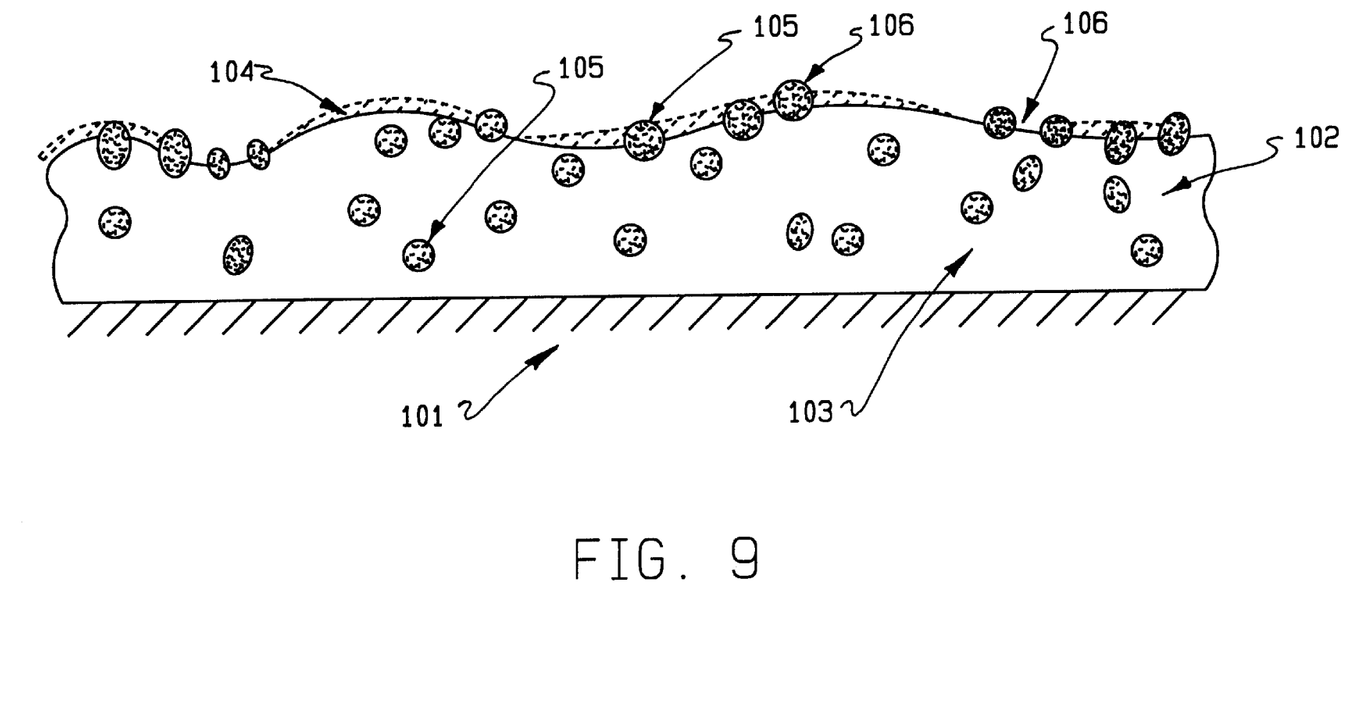
FIG. 9 illustrates a surface of an implantable prosthesis covered with an undercoat, containing a biologically active material, which is partly covered by a topcoat.

This mechanism is illustrated by FIG. 9, which shows a surface of a prosthesis 101 covered by a coating 102 comprising an undercoat 103 and a topcoat 104. The topcoat 104, which only partially covers the undercoat 103, leaves certain areas 106 of the undercoat, including drug particles 105, exposed to body fluids at the implantation site. It is through these "uncovered" areas 106 of the undercoat that the drug particles 105 of the undercoat 103 are allowed to be released into the implantation site.

Additionally, it is preferred that the topcoats have an average thickness equivalent to the average particle size of the drug in the undercoat. Preferably the average thickness is about 1 to 7 microns and more preferable that the topcoat average thickness be about 1 to 5 microns. Also, the polymer of the topcoat may be the same as or different from the polymer of the undercoat.

The coating may be applied by dipping or spraying using evaporative solvent materials of relatively high vapor pressure to produce the desired viscosity and quickly establish coating layer thicknesses. The preferred process is predicated on reciprocally spray coating a rotating radially expanded stent employing an air brush device. The coating process enables the material to adherently conform to and cover the entire surface of the filaments of the open structure of the stent but in a manner such that the open lattice nature of the structure of the braid or other pattern is preserved in the coated device.

The coating is exposed to room temperature ventilation for a predetermined time (possibly one hour or more) for solvent vehicle evaporation. In the case of certain undercoat materials, thereafter the polymer material is cured at room temperature or elevated temperatures. Curing is defined as the process of converting the elastomeric or polymeric material into the finished or useful state by the application of heat and/or chemical agents which induce physico-chemical changes. Where, for example, polyurethane thermoplastic elastomers are used as an undercoat material, solvent evaporation can occur at room temperature rendering the undercoat useful for controlled drug release without further curing.

The applicable ventilation time and temperature for cure are determined by the particular polymer involved and particular drugs used. For example, silicone or polysiloxane materials (such as polydimethylsiloxane) have been used successfully. Urethane prepolymers can also be utilized. Unlike the polyurethane thermoplastic elastomers, some of these materials are applied as prepolymers in the coating composition and must thereafter be heat cured. The preferred silicone species have a relatively low cure temperatures and are known as a room temperature vulcanizable (RTV) materials. Some polydimethylsiloxane materials can be cured, for example, by exposure to air at about 90° C. for a period of time such as 16 hours. A curing step may be implemented both after application of the undercoat or a certain number of lower layers and the top layers or a single curing step used after coating is completed.

The coated stents may thereafter be subjected to a post-cure process which includes an inert gas plasma treatment, and sterilization which may include gamma radiation, ETO treatment, electron beam or steam treatment.

In the plasma treatment, unconstrained coated stents are placed in a reactor chamber and the system is purged with nitrogen and a vacuum applied to 20–50 mTorr. Thereafter, inert gas (argon, helium or mixture of them) is admitted to the reaction chamber for the plasma treatment. One method uses argon (Ar) gas, operating at a power range from 200 to 400 watts, a flow rate of 150–650 standard ml per minute, which is equivalent to about 100–450 mTorr, and an exposure time from 30 seconds to about 5 minutes. The stents can be removed immediately after the plasma treatment or remain in the argon atmosphere for an additional period of time, typically five minutes.

In accordance with the invention, the topcoat or surface coating may be applied in any of several ways to further control thrombolytic effects and optionally, control the release profile especially the initial very high release rate associated with the elution of heparin.

In one embodiment, an outer layer of fluorosilicone (FSi) is applied to the undercoat as a topcoat. The outer layer can also contain heparin. In another embodiment, polyethylene glycol (PEG) is immobilized on the surface of the coating. In this process, the underlayer is subjected to inert gas plasma treatment and immediately thereafter is treated by ammonia ($NH_3$) plasma to aminate the surface. Amination, as used in this application, means creating mostly imino groups and other nitro containing species on the surface. This is followed by immediate immersion into electrophilically activated polyethylene glycol(PEG) solution with a reductive agent, i.e., sodium cyanoborohydride.

To form a topcoat which is substantially free of pores, porosigens or materials capable of eluting from the topcoat during implantation, should not be included in the composition used to form the topcoat. For example, a substantially non-porous topcoat can be produced from a topcoat composition which comprises a substantially pure polymeric material. The material preferably provides biocompatibility to the implanted device during and after release of the biologically active material.

To prepare a topcoat which covers less than the entire surface of the undercoat, a number of methods can be used. For instance, by controlling the thickness of the topcoat so that it has an average thickness less than that of the diameter of certain drug particles, the undercoat will be only partly covered by the topcoat since some of drug particles will not be covered by the topcoat.

Also, a partial topcoat can be formed by using a topcoat polymer which is incompatible with the undercoat polymer to generate a microphase separation in the topcoat. Furthermore, to make a topcoat which covers less than the entire surface of the undercoat or which only partially covers the undercoat, a poor solvent wash can be applied to the topcoat, to force the topcoat polymer to shrink so that the undercoat is not entirely covered.

In other embodiments the topcoat can partially or fully cover the undercoat prior to delivery or implantation of the device. The topcoat materials can be selected so they have certain water permeability. When water penetrates the topcoat and into the drug particles of the undercoat, the water will swell the particles or dissolve the particles. In either situation, it creates osmotic pressure in the surrounding coating material of the undercoat. The pressure then breaks the thinnest part of the topcoat, and leave the void space in the topcoat for the drug to elute out.

In another embodiment, the topcoat material has a different Young's modulus (either while it is wet or dry) than that of the undercoat material. More specifically, the Young's modulus can be higher for the topcoat material. During the mounting of the coated devices onto the delivery device or during deployment of the coated device, the coating undergoes compression or stretching. Topcoat materials with higher Young's modulus tend to crack and form void spaces for the drug to elute from undercoat.

Another way to form a topcoat is to cover the undercoat with a bioabsorbable material. In this embodiment, the topcoat can cover either the entire undercoat or only part of the undercoat before or after implantation. Upon contact with body fluids, the bioabsorbable material of the topcoat will degrade. The rate of degradation depends upon the bioabsorbable material used. When the topcoat is partially absorbed, the undercoat is exposed to the body fluid and the drug is released, however the burst effect will be reduced.

The coated and cured stents having the modified outer layer or surface optionally are subjected to a final gamma radiation sterilization nominally at 2.5–3.5 Mrad. Argon (Ar) plasma treated stents enjoy full resiliency after radiation whether exposed in a constrained or non-constrained status, while constrained stents subjected to gamma sterilization without Ar plasma pretreatment lose resiliency and do not recover at a sufficient or appropriate rate where the undercoat is silicone.

The elastomeric materials that form the stent coating underlayers should possess certain properties. Preferably the layers should be of suitable hydrophobic biostable elastomeric materials which do not degrade. Surface layer or topcoat materials should minimize tissue rejection and tissue inflammation and permit encapsulation by tissue adjacent the stent implantation site. Exposed material is designed to reduce clotting tendencies in blood contacted and the surface is preferably modified accordingly. Thus, undarlayarg of the above materials are preferably provided with a silicone or a fluorosilicone outer coating layer which should not contain imbedded bioactive material, such as heparin in order to avoid the formation of pores in the topcoat. Alternatively, the outer coating may consist essentially of polyethylene glycol (PEG), polysaccharides, phospholipids, or combinations of the foregoing.

Polymers generally suitable for the undercoats or underlayers include silicones (e.g., polysiloxanes and substituted polysiloxanes), polyurethanes, thermoplastic elastomers in general, ethylene vinyl acetate copolymers, polyolefin elastomers, polyamide elastomers, and EPDM rubbers. The above-referenced materials are considered hydrophobic with respect to the contemplated environment of the invention. Surface layer or topcoat materials can include the same polymer as that of the undercoat. Examples of suitable polymers include without limitation fluorosilicones and polyethylene glycol (PEG), polysaccharides, phospholipids, and combinations of the foregoing.

While heparin is preferred as the incorporated active material, agents possibly suitable for incorporation include antithrobotics, anticoagulants, antibiotics antiplatelet agents, thrombolytics, antiproliferatives, steroidal and nonsteroidal antiinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.q., endothelium) and tissue formation (neointimal tissue).

Suitable materials for fabricating the braided stent include stainless steel, tantalum, titanium alloys including nitinol (a nickel titanium, thermomemoried alloy material), and certain cobalt alloys including cobalt-chromium-nickel alloys such as Elgiloy® and Phynox®. Further details concerning the fabrication and details of other aspects of the stents themselves, may be gleaned from the above referenced U.S. Pat. Nos. 4,655,771 and 4,954,126 to Wallsten and U.S. Pat. No. 5,061,275 to Wallsten et al., which are incorporated by reference herein.

Various combinations of polymer coating materials can be coordinated with biologically active species of interest to produce desired effects when coated on stents to be implanted in accordance with the invention. Loadings of therapeutic materials may vary. The mechanism of incorporation of the biologically active species into the surface coating, and egress mechanism depend both on the nature of the surface coating polymer and the material to be incorporated. The mechanism of release also depends on the mode of incorporation. The material may elute via interparticle paths or be administered via transport or diffusion through the encapsulating material itself.

For the purposes of this specification, "elution" is defined as any process of release that involves extraction or release by direct contact of the material with bodily fluids through the interparticle paths connected with the exterior of the coating. "Transport" or "diffusion" are defined to include a mechanism of release in which the material released traverses through another material.

The desired release rate profile can be tailored by varying the coating thickness, the radial distribution (layer to layer) of bioactive materials, the mixing method, the amount of bioactive material, the combination of different matrix polymer materials at different layers, and the crosslink density of the polymeric material. The crosslink density is related to the amount of crosslinking which takes place and also the relative tightness of the matrix created by the particular crosslinking agent used. This, during the curing process, determines the amount of crosslinking and so the crosslink density of the polymer material. For bioactive materials released from the crosslinked matrix, such as heparin, a denser crosslink structure will result in a longer release time and reduced burst effect.

It will also be appreciated that an unmedicated silicone thin top layer provides some advantage and additional control over drug elution.

BRIEF DESCRIPTION OF THE DRAWINGS

In the drawings, wherein like numerals designate like parts throughout the same.

DETAILED DESCRIPTION

According to the present invention, the stent coatings incorporating biologically active materials for timed delivery in situ in a body lumen of interest are preferably sprayed in many thin layers from prepared coating solutions or suspensions. The steps of the process are illustrated generally in FIG. 1. The coating solutions or suspensions are prepared at 10 as will be described later. The desired amount of crosslinking agent (if any) is added to the suspension/solution as at 12 and material is then agitated or stirred to produce a homogenous coating composition at 14 which is thereafter transferred to an application container or device which may be a container for spray painting at 16. Typical exemplary preparations of coating solutions that were used for heparin and dexamethasone appear next.

General Preparation of Heparin Undercoating Composition

Silicone was obtained as a polymer precursor in solvent (xylene) mixture. For example, a 35% solid silicone weight content in xylene was procured from Applied Silicone, Part #40,000. First, the silicone-xylene mixture was weighed. The solid silicone content was determined according to the vendor's analysis. Precalculated amounts of finely divided heparin (2–6 microns) were added into the silicone, then tetrahydrofuran (THF) HPCL grade (Aldrich or EM) was added.

For a 37.5% heparin coating, having 35% solids, $W_{silicone}=5$ g and $W_{hep}=5\times0.35\times0.375/(0.625)=1.05$ g were used. The amount of THF needed (44 ml) in the coating solution was calculated by using the equation $W_{silicone\ solid}/V_{THF}=0.04$ for a 37.5% heparin coating solution. Finally, the manufacturer crosslinker solution was added by using Pasteur P-pipet. The amount of crosslinker added was formed to effect the release rate profile. Typically, five drops of crosslinker solution were added for each five grams of silicone-xylene mixture. The solution was stirred by using the stirring rod until the suspension was homogenous and milk-like. The coating solution was then transferred into a paint jar in condition for application by air brush.

General Preparation of Dexamethasone Undercoating Composition

Silicone (35% solution as above) was weighed into a beaker on a Metler balance. The weight of dexamethasone free alcohol or acetate form was calculated by silicone weight multiplied by 0.35 and the desired percentage of dexamethasone (1 to 40%) and the required amount was then weighed. Example: $W_{silicone}=5$ g; for a 10% dexamethasone coating, $W_{dex}=5\times0.35\times0.1/0.9=0.194$ g and THF needed in the coating solution and $W_{silicone\ solid}/V_{THF}=0.06$ for a 10% dexamethasone coating solution. Example: $W_{silicone}=5$ g; $V_{THF}=5\times0.35/0.06\approx29$ ml. The dexamethasone was weighed in a beaker on an analytical balance and half the total amount of THF wag added. The solution was stirred well to ensure full dissolution of the dexamethasone. The stirred DEX-THF solution was then transferred to the silicone container. The beaker was washed with the remaining THF and this was transferred to the silicone container. The crosslinker was added by using a Pasteur pipet. Typically, five drops of crosslinker were used for five grams of silicone.

The application of the coating material to the stent was quite similar for all of the materials and the same for the heparin and dexamethasone suspensions prepared as in the above Examples. The suspension to be applied was transferred to an application device, at 16 in FIG. 1. Typically a paint jar attached to an air brush, such as a Badger Model 150, supplied with a source of pressurized air through a regulator (Norgren, 0–160 psi) was used. Once the brush hose was attached to the source of compressed air downstream of the regulator, the air was applied. The pressure was adjusted to approximately 15–25 psi and the nozzle condition checked by depressing the trigger.

To secure the stent for spraying and rotating fixtures were utilized successfully in the laboratory. Both ends of the relaxed stent were fastened to the fixture by two resilient retainers, commonly alligator clips, with the distance between the clips adjusted so that the stent remained in a relaxed, unstretched condition. The rotor was then energized and the spin speed adjusted to the desired coating speed, nominally about 40 rpm.

With the stent rotating in a substantially horizontal plane, the spray nozzle was adjusted so that the distance from the nozzle to the stent was about 2–4 inches and the composition was sprayed substantially horizontally with the brush being directed along the stent from the distal end of the stent to the proximal end and then from the proximal end to the distal end in a sweeping motion at a speed such that one spray cycle occurred in about three stent rotations. Typically a pause of less than one minute, normally about one-half minute, elapsed between layers. Of course, the number of coating layers did and will vary with the particular application. For example, typical tie-layers as at 18 in FIG. 1, for a coating level of 3–4 mg of heparin per $cm^2$ of projected area, 20 cycles of coating application are required and about 30 ml of solution will be consumed for a 3.5 mm diameter by 14.5 cm long stent.

The rotation speed of the motor, of course, can be adjusted as can the viscosity of the composition and the flow rate of the spray nozzle as desired to modify the layered structure. Generally, with the above mixes, the best results have been obtained at rotational speeds in the range of 30–50 rpm and with a spray nozzle flow rate in the range of 4–10 ml of coating composition per minute, depending on the stent size. It is contemplated that a more sophisticated, computer-controlled coating apparatus will successfully automate the process demonstrated as feasible in the laboratory.

Figure 1:
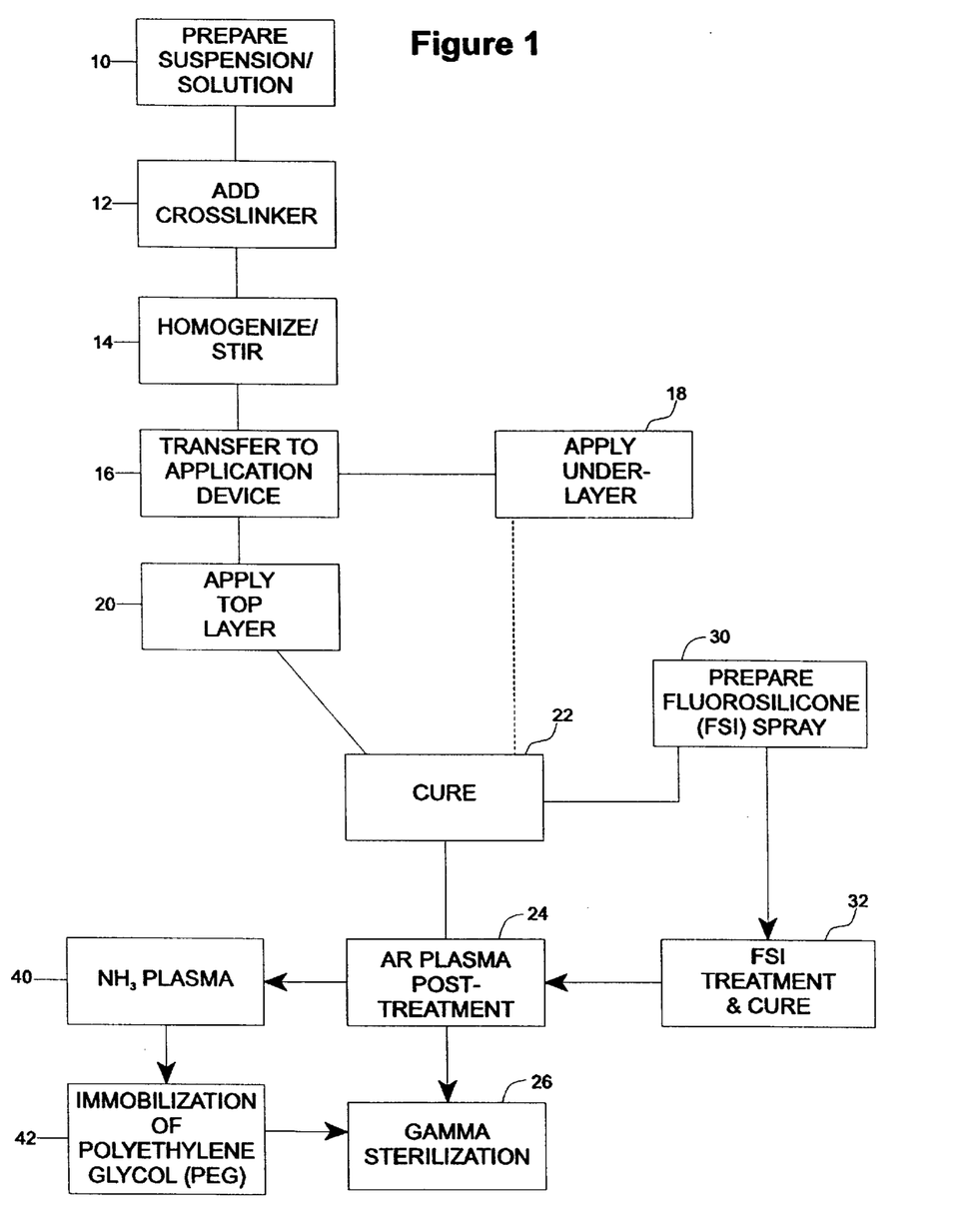
FIG. 1 is a schematic flow diagram illustrating the steps of the process of the invention.
Figure 2:
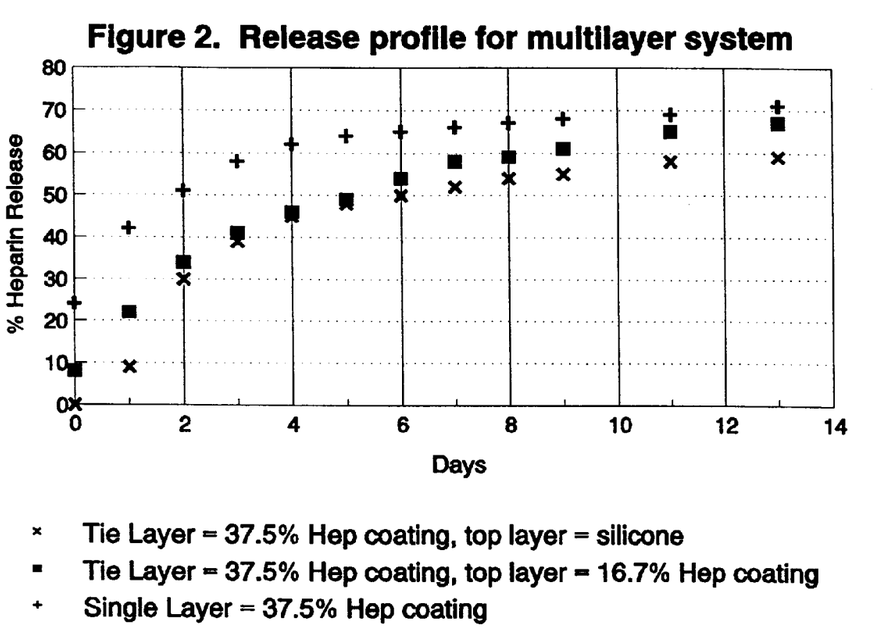
FIG. 2 represents a release profile for a multi-layer system showing the percentage of heparin released over a two-week period.
Figure 3:
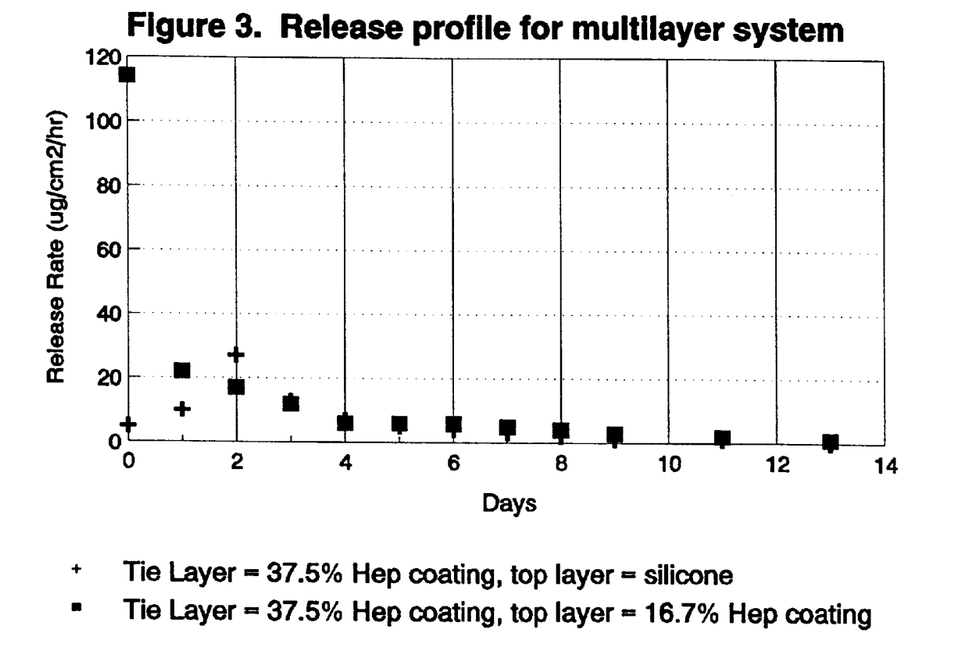
FIG. 3 represents a release profile for a multi-layer system showing the relative release rate of heparin over a two-week period.

Several applied layers make up what is called the undercoat as at 18. In one process, additional upper undercoat layers, which may be of the same or different composition with respect to bioactive material, the matrix. polymeric materials and crosslinking agent, for example, may be applied as the top layer as at 20. The application of the top layer follows the same coating procedure as the undercoat with the number and thickness of layers being optional. of course, the thickness of any layer can be adjusted by adjusting the speed of rotation of the stent and the spraying conditions. Generally, the total coating thickness is controlled by the number of spraying cycles or thin coats which make up the total coat.

As shown at 22 in FIG. 1, the coated stent is thereafter subjected to a curing step in which the prepolymer and crosslinking agents cooperate to produce a cured polymer matrix containing the biologically active species. The curing process involves evaporation of the solvent xylene, THF, etc. and the curing and crosslinking of the polymer. Certain silicone materials can be cured at relatively low temperatures, (i.e., RT-50° C.) in what is known as a room temperature vulcanization (RTV) process. More typically, however, the curing process involves higher temperature curing materials and the coated stents are put into an oven at approximately 90° C. or higher for approximately 16 hours. The temperature may be raised to as high as 150° C. for dexamethasone containing coated stents. Of course, the time and temperature may vary with particular silicones, crosslinkers and biologically active species.

Stents coated and cured in the manner described need to be sterilized prior to packaging for future implantation. For sterilization, gamma radiation is a preferred method particularly for heparin containing coatings; however, it has been found that stents coated and cured according to the process of the invention subjected to gamma sterilization may be too slow to recover their original posture when delivered to a vascular or other lumen site using a catheter unless a pretreatment step as at 24 is first applied to the coated, cured stent.

The pretreatment step involves an argon plasma treatment of the coated, cured stents in the unconstrained configuration. In accordance with this procedure, the stents are placed in a chamber of a plasma surface treatment system such as a Plasma Science 350 (Himont/Plasma Science, Foster City, Calif.). The system is equipped with a reactor chamber and RF solid-state generator operating at 13.56 mHz and from 0–500 watts power output and being equipped with a microprocessor controlled system and a complete vacuum pump package. The reaction chamber contains an unimpeded work volume of 16.75 inches (42.55 cm) by 13.5 inches (34.3 cm) by 17.5 inches (44.45 cm) in depth.

In the plasma process, unconstrained coated stents are placed in a reactor chamber and the system is purged with nitrogen and a vacuum applied to 20–50 mTorr. Thereafter, inert gas (argon, helium or mixture of them) is admitted to the reaction chamber for the plasma treatment. A highly preferred method of operation consists of using argon gas, operating at a power range from 200 to 400 watts, a flow rate of 150–650 standard ml per minute, which is equivalent to 100–450 mTorr, and an exposure time from 30 seconds to about 5 minutes. The stents can be removed immediately after the plasma treatment or remain in the argon atmosphere for an additional period of time, typically five minutes.

After this, as shown at 26, the stents may be exposed to gamma sterilization at 2.5–3.5 Mrad. The radiation may be carried out with the stent in either the radially unconstrained status or in the radially constrained status.

Preferably, however, the surface is modified prior to plasma treatment or just prior to sterilization by one of several additional processing methods of which some are described in relation to the following examples.

EXAMPLE 1
Fluorosilicone Surface Treatment of Eluting Heparin Coating

The undercoat of a stent was coated as multiple applied layers as described above thereafter and cured as described at 22. The heparin content of the undercoat was 37.5% and the coating thickness was about 30–40 $\mu$. Fluorosilicone (FSi) spray solution was prepared at 30 from a fluorosilicone suspension (Applied Silicone #40032) by weighing an amount of fluorosilicone suspension and adding tetrahydrofuran (THF) according to the relation equation of $V_{THF}$= 1.2×the weight of fluorosilicone suspension. The solution was stirred very well and spray-coated on the stent at 32 using the technique of the application of the undercoat process at 18 and the coated stents were cured at 90° C. for 16 hours. The coated stents are argon plasma treated prior to gamma sterilization according to the procedures described above in accordance with steps 22–26.

Figure 7:
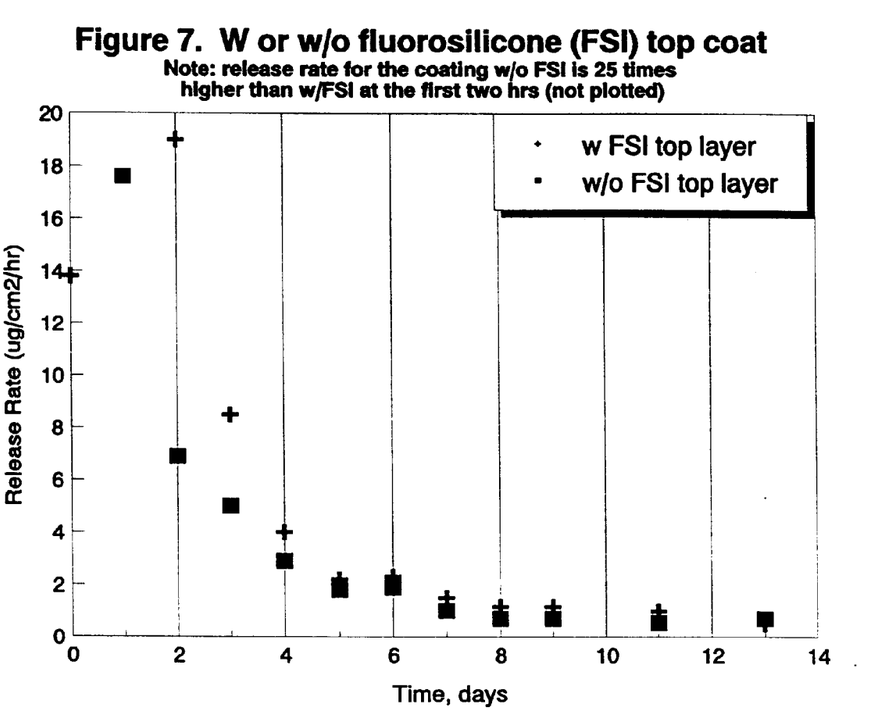
FIG. 7 is a plot of heparin release kinetics in phosphate buffer system at pH 7.4 with and without fluorosilicone (FSi) topcoat.

FIG. 7 is a plot of heparin release kinetics in phosphate buffer system with fluorosilicone topcoat and without any topcoat. The thickness of the topcoat is about 10–15 A. While it does not appear on the graph of FIG. 7, it should be noted that the release rate for the coating without FSi is initially about 25 times higher than that with FSi, i.e., during the first 2 hours. This is, of course, clearly off the scale of the graph. It is noteworthy, however, that the coating with the FSi top layer or diffusion barrier does show a depressed initial release rate combined with an enhanced elution rate after the first day and through the first week up until about the tenth day. In addition, the fluorosilicone (FSi) topcoat, by virtue of the high electronegativity of fluorination maintains non-thrombogenic surface qualities during and after the elusion of the biologically active heparin species. In addition, because of the negative charges off the heparin itself, the electro-negativity of the fluorosilicone topcoat may be, at least in part, responsible for the modified heparin release kinetic profile.

Figure 8:
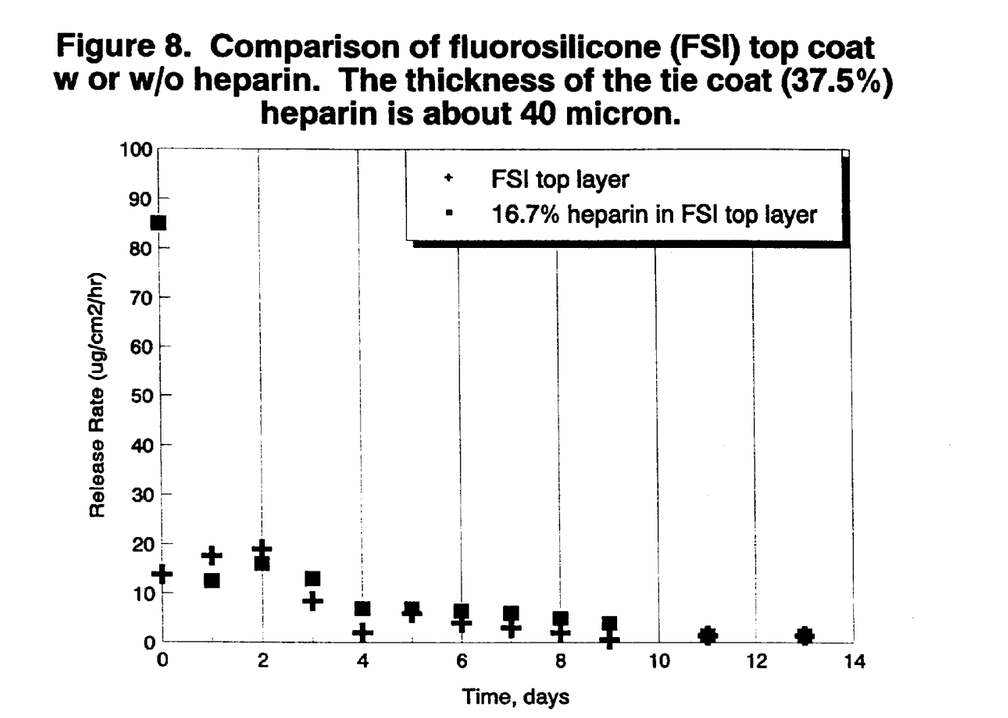
FIG. 8 is another plot of heparin release kinetics in phosphate buffer system in which a topcoat containing fluorosilicone (FSi) only is compared with an FSi topcoat containing 16.7% imbedded heparin.

FIG. 8 compares a plot of fluorosilicone (FSi) top coating containing 16.7% imbedded heparin with one containing fluorosilicone (FSi) only. An undercoating is identical to that utilized in FIG. 7 containing about 37.5% heparin to a thickness of about 30–40 microns. These elution kinetics are quite comparable with the heparin-free FSi top layer greatly reducing the initial burst of heparin release and otherwise the heparin in the FSi top layer imparts a slightly greater release over the period of the test.

EXAMPLE 2
Immobilization of Polyethylene Glycol (PEG) on Drug Eluting Undercoat

An undercoat was coated on a stent and cured at 22 as in Example 1. The stent was then treated by argon gas plasma as at 24 and ammonium gas plasma at 40. The equipment and the process of argon gas plasma treatment was as has been described above. The ammonium plasma treatment was implemented immediately after the argon gas plasma treatment, to aminate the surface of the coating. The ammonium flow rate was in the range of 100–700 cubic centimeter per minute (ccM) in preferably in the range of 500–600 ccM. The power output of radio frequency plasma was in the range of 50–500 watts, preferably in ~200 watts. The process time was in the range of 30 sec–10 min, preferably ~5 min.

Immediately after amination, the stents were immersed into electrophilically activated polyethylene glycol (PEG) solution it 42. PEG is known to be an inhibitor of protein absorption. Examples of electrophilically activated PEG are PEG nitrophenyl carbonates, PEG trichlorophenyl carbonates, PEG tresylate, PEG glycidyl ether, PEG isocyanate, etc., optionally with one end terminated with methoxyl group. Molecular weight of PEG ranged from about 1000–6000, and is preferable about 3000. It has been observed that simple ammonium amination will not generate large quantities of primary and secondary amines on the elastomeric polymer surface (for example silicone). Instead, imine (>C=N—H), and other more oxidative nitro containing groups will dominate the surface. It is generally necessary to add reductive agent, such as $NaBH_3CN$ into the reaction media so that the functional group on PEG can react with imine and possibly other nitro-containing species on the surface, and therefore immobilize PEG onto the surface. The typical concentration of $NaBH_3CN$ is about 2 mg/ml. Since PEG and its derivatives dissolve in water and many polar and aromatic solvents, the solvent used in the coating must be a solvent for PEG but not for the drug in the undercoat to prevent the possible loss of the drug through leaching. In the case of eluting-heparin coating, a mixed solvent of formamide and methyl ethyl ketone (MEK) or a mixed solvent of formamide and acetone are preferred solvents, (preferably at ratios of 30 formamide:70 MEK or acetone by volume), since they will not dissolve heparin. The concentration of PEG, the reaction time, the reaction temperature and the pH value depend on the kind of PEG employed. In the case of eluting heparin coating, 5% PEG tresylate in (30–70) Formamide/MEK was used successfully. The reaction time was 3 hours at room temperature. PEG was then covalently bound to the surface. Gamma radiation was then used for sterilization of this embodiment as previously described.

With respect to the anticoagulant material heparin, the percentage in the undercoat is nominally from about 30–50% and that of the topcoat from about 0–30% active material. The coating thickness ratio of the topcoat to the undercoat varies from about 1:10 to 1:2 and is preferably in the range of from about 1:6 to 1:3.

To produce a topcoat which is substantially free of pores, materials such as porosigens, which can be removed or leached out of the topcoat should not be included in the composition used to form the topcoat. One way of preparing a substantially non-porous topcoat is to apply a topcoat composition which comprises substantially pure polymeric materials. These materials preferably impart biocompatibility to the implanted device during and after the release of the biologically active material.

A topcoat which only partially covers the undercoat can be formed in a number of ways. Such methods include controlling the thickness of the topcoat so that it is less than the diameter of certain drug particles in the undercoat. For example, when a drug used in the undercoat has an average particle size of 5 µm, it is possible that 15% of the particles will be greater than or equal to 8 µm. At the molecular level, the surface unevenness is at least more than 5 microns. By application of a topcoat of about 5 micron or less. The uneven surface will become smooth to a certain degree. But uncovered areas will still exist, which allows water to penetrate into the undercoat, swelling the drug particle, or dissolving the drug. Due to the osmotic pressure, the drug will elute out through the uncovered areas. If the osmotic pressure is too high, cracks or voids may form in the topcoat which allows drugs to elute from the undercoat to the body.

As illustrated in FIG. 9, in a coating 102 which covers a surface of a prosthesis 101, a thin topcoat 104 of the coating 102 only partially covers the undercoat 103 of the coating 102. By having the topcoat 104 cover less than the entire surface of the undercoat 103, parts of the undercoat 103, including a number of drug particles 105, are exposed to body fluids at the implantation site so that the drug 105 can be released. By using a topcoat 104 having a thickness which is about the average particle size of the drug 105, certain larger sized drug particles 106 will not be covered by the topcoat 104.

Other methods to form a partially covered topcoat include using a polymer which is incompatible to the undercoat elastomer as the biocompatible material of the topcoat. Because of the incompatibility between the materials, a microphase separation will form in the topcoat which will leave the undercoat partially uncovered. Persons skilled in the art are aware of suitable combinations of such incompatible materials.

Another method involves applying a poor solvent wash to the topcoat to force the biocompatible polymer to shrink and create uneven surfaces voids in the topcoat which forms a topcoat which partially covers the undercoat.

In yet another method of making a topcoat which partly or fully covers the undercoat, topcoat and undercoat materials having different Young's moduli (either before or after they have cured) are used. For instance, a topcoat material having a higher Young's modulus compared to that of the undercoat material can be employed. When the coated device is mounted on the delivery device or during deployment of the coated device, the topcoat undergoes compression or stretching or other types of mechanical challenges. Since the topcoat material has a higher Young's modulus, it will tend to crack and form voids in the topcoat to allow the drug of the undercoat to elute therefrom.

Another method for forming the topcoat involves using a bioabsorbable material in the topcoat, which can cover the entire undercoat or only a part of the undercoat. When the coated device comes into contact with body fluid, the topcoat begins to degrade either at the surface or throughout the bulk of the topcoat. The rate of degradation depends upon the type of bioabsorbable material used. Once the topcoat has been partially absorbed, the undercoat is exposed to body tissue and the drug in the undercoat is released, but the burst release or effect is reduced.

Suppressing the burst effect also enables a reduction in the drug loading or in other words, allows a reduction in the coating thickness, since the physician will give a bolus injection of antiplatelet/anticoagulation drugs to the patient during the stenting process. As a result, the drug imbedded in the stent can be fully used without waste. Tailoring the first day release, but maximizing second day and third day release at the thinnest possible coating configuration will reduce the acute or subacute thrombosis particularly if drugs such as heparin are incorporated.

Figure 4:
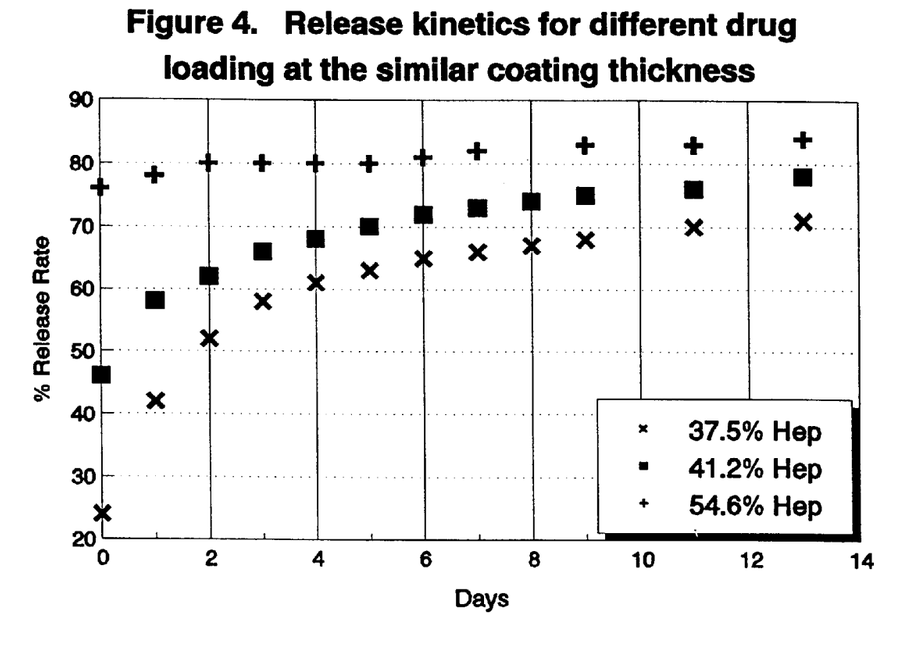
FIG. 4 illustrates a profile of release kinetics for different drug loadings at similar coating thicknesses illustrating the release of heparin over a two-week period without associated means to provide a long term non-thrombogenic surface thereafter.
Figure 5:
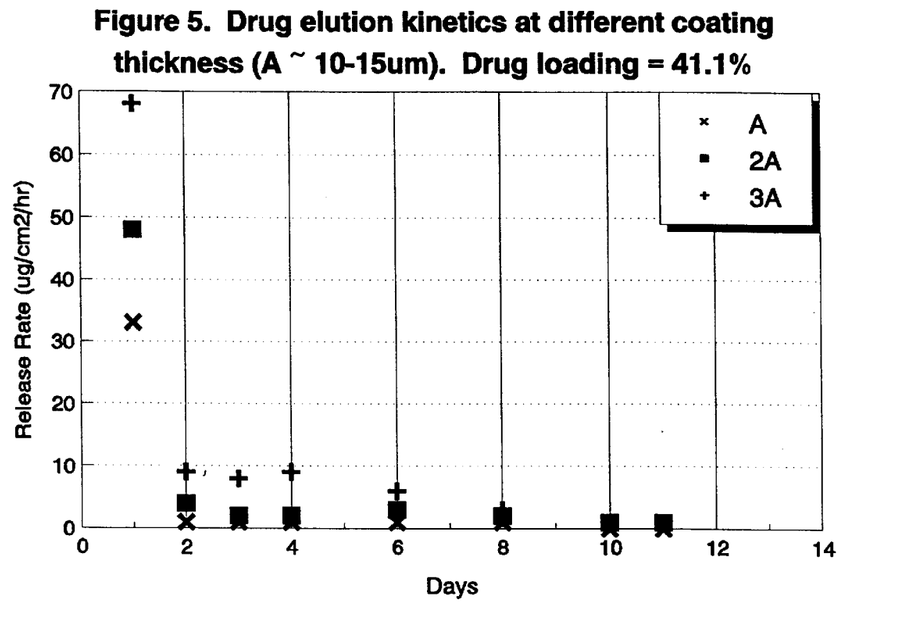
FIG. 5 illustrates drug elution kinetics at a given loading of heparin over a two-week period at different coating thicknesses without associated means to provide a long term non-thrombogenic surface thereafter.
Figure 6:
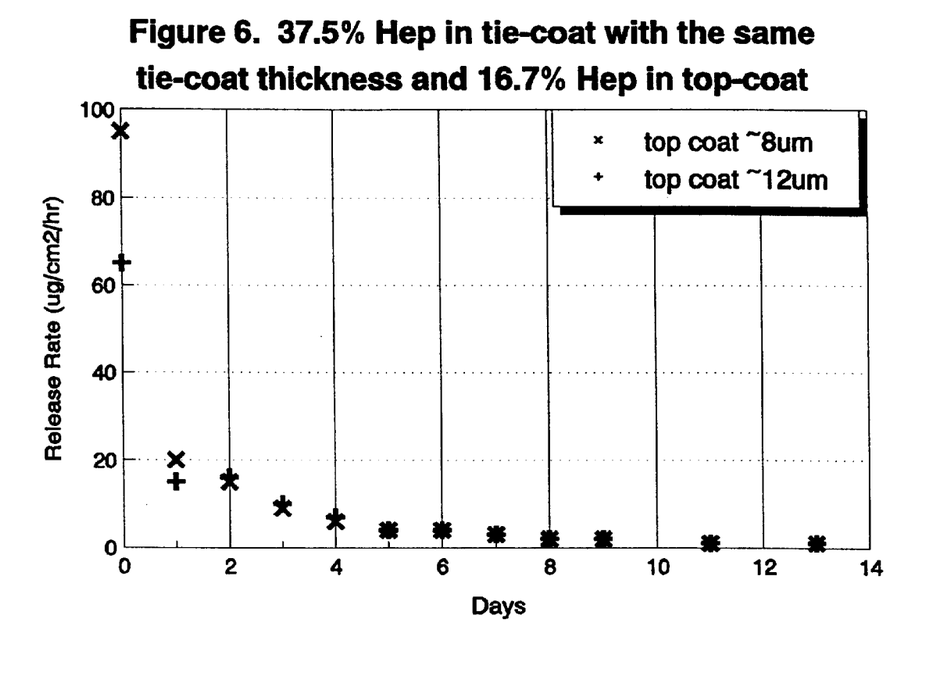
FIG. 6 illustrates the release kinetics for a given undercoat and topcoat material varied according to thickness in which the percentage heparin in the undercoat and topcoats are kept constant.

FIG. 4 depicts the general effect of drug loading for coatings of similar thickness. The initial elution rate increases with the drug loading as shown in FIG. 5. The release rate also increases with the thickness of the coating at the same loading but tends to be inversely proportional to the thickness of the topcoat as shown by the same drug loading and similar undercoat thickness in FIG. 6.

What is apparent from the data gathered to date, however, is that the process of the present invention enables the drug elution kinetics to be controlled in a manner desired to meet the needs of the particular stent application. In a similar manner, stent coatings can be prepared using a combination of two or more drugs and the drug release sequence and rate controlled. For example, antiproliferation drugs may be combined in the undercoat and antiplatelet drugs in the topcoat. In this manner, the antiplatelet drugs, for example, heparin, will elute first followed by antiproliferation drugs to better enable safe encapsulation of the implanted stent.

The heparin concentration measurement were made utilizing a standard curve prepared by complexing azure A dye with dilute solutions of heparin. Sixteen standards were used to compile the standard curve in a well-known manner.

For the elution test, the stents were immersed in a phosphate buffer solution at pH 7.4 in an incubator at approximately 37° C. Periodic samplings of the solution were processed to determine the amount of heparin eluted. After each sampling, each stent was placed in heparin-free buffer solution.

As stated above, while the allowable loading of the elastomeric material with heparin may vary, in the case of silicone materials, heparin may exceed 60% of the total weight of the layer. However, the loading generally most advantageously used is in the range from about 10% to 45% of the total weight of the layer. In the case of dexamethasone, the loading may be as high as 50% or more of the total weight of the layer but is preferably in the range of about 0.4% to 45%.

It will be appreciated that the mechanism of incorporation of the biologically active species into a thin surface coating structure applicable to a metal stent is an important aspect of the present invention. The need for relatively thick-walled polymer elution stents or any membrane overlayers associated with many prior drug elution devices is obviated, as is the need for utilizing biodegradable or reabsorbable vehicles for carrying the biologically active species. The technique clearly enables long-term delivery and minimizes interference with the independent mechanical or therapeutic benefits of the stent itself.

Coating materials are designed with a particular coating technique, coating/drug combination and drug infusion mechanism in mind. Consideration of the particular form and mechanism of release of the biologically active species in the coating allow the technique to produce superior results. In this manner, delivery of the biologically active species from the coating structure can be tailored to accommodate a variety of applications.

Whereas the above examples depict coatings having two different drug loadings or percentages of biologically active material to be released, this is by no means limiting with respect to the invention and it is contemplated that any number of layers and combinations of loadings can be employed to achieve a desired release profile. For example, gradual grading and change in the loading of the layers can be utilized in which, for example, higher loadings are used in the inner layers. Also layers can be used which have no drug loadings at all. For example, a pulsatile heparin release system may be achieved by a coating in which alternate layers containing heparin are sandwiched between unloaded layers of silicone or other materials for a portion of the coating. In other words, the invention allows untold numbers of combinations which result in a great deal of flexibility with respect to controlling the release of biologically active materials with regard to an implanted stent. Each applied layer is typically from approximately 0.5 microns to 15 microns in thickness. The total number of sprayed layers, of course, can vary widely, from less than 10 to more than 50 layers; commonly, 20 to 40 layers are included. The total thickness of the coating can also vary widely, but can generally be,from about 10 to 200 microns.

Whereas the polymer of the coating may be any compatible biostable elastomeric material capable of being adhered to the stent material as a thin layer, hydrophobic materials are preferred because it has been found that the release of the biologically active species can generally be more predictably controlled with such materials. Preferred materials include silicone rubber elastomers and biostable polyurethanes specifically.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

We claim:

1. A method of coating an implantable stent prosthesis having at least a portion which is implantable into the body of a patient, wherein at least a part of the stent portion is covered with a coating for release of at least one biologically active material; the method comprising:
   (a) applying an undercoat comprising a polymeric material and the biologically active material to the stent portion wherein the undercoat has a surface; and
   (b) applying a discontinuous topcoat which covers less than the entire surface of the undercoat, said topcoat comprising a polymeric material, substantially free of pores and pore-forming materials.

2. The method of claim 1 wherein the polymeric material of the undercoat is a hydrophobic elastomeric material and wherein the polymeric material of the undercoat is a biostable, biocompatible material which provides long term non-thrombogenicity to the stent portion during and after release of the biologically active material.

3. The method of claim 1 wherein the polymeric material of the topcoat is selected from the group consisting of fluorosilicone, polyethylene glycol (PEG), polysaccharides, phospholipids and combinations thereof.

4. The method of claim 1 wherein the topcoat covers from about 5% to 95% of the surface of the undercoat.

5. The method of claim 4 wherein the topcoat covers from about 20% to 85% of the surface of the undercoat.

6. The method of claim 1 wherein the topcoat has an average thickness of about the average particle size of the biologically active material.

7. The method of claim 1 wherein the topcoat has an average thickness of about 1 to 7 microns.

8. The method of claim 7 wherein the topcoat has an average thickness of about 1 to 5 microns.

9. The method of claim 1 wherein the polymeric material of the topcoat is a polymer which is incompatible with the polymeric material of the undercoat such that the discontinuous topcoat is formed.

10. The method of claim 1 which further comprises applying a poor solvent to the topcoat to shrink the polymeric material to form the discontinuous topcoat.

11. The method of claim 1 wherein the Young's modulus of the polymeric material of the undercoat and the Young's modulus of the polymeric material of the topcoat are different.

12. The method of claim 11 wherein the Young's modulus of the polymeric material of the topcoat is greater than the Young's modulus of the polymeric material of the undercoat.

* * * * *